US00PP28515P3

(12) United States Plant Patent
Beekenkamp

(10) Patent No.: US PP28,515 P3
(45) Date of Patent: Oct. 10, 2017

(54) ***BEGONIA* PLANT NAMED 'BKPBEEEBP'**

(50) Latin Name: *Begonia×hiemalis*
Varietal Denomination: BKPBEEEBP

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk, NC (US)

( * ) Notice: Subject to any disclaimer, the term of this patent is extended or adjusted under 35 U.S.C. 154(b) by 13 days.

(21) Appl. No.: 14/998,880

(22) Filed: Feb. 25, 2016

(65) Prior Publication Data

US 2017/0251581 P1 Aug. 31, 2017

(51) Int. Cl.
*A01H 5/02* (2006.01)

(52) U.S. Cl.
USPC ..... Plt./349

(58) Field of Classification Search
USPC ..... Plt./349
See application file for complete search history.

*Primary Examiner* — Keith Robinson
(74) *Attorney, Agent, or Firm* — C. A. Whealy

(57) ABSTRACT

A new and distinct cultivar of *Begonia* plant named 'BKPBEEEBP', characterized by its broadly upright to outwardly spreading and mounded plant habit; freely basal branching habit; dark green-colored leaves; uniform and freely flowering habit; and semi-double to fully double flowers with tepals and tepaloids that are bright red purple in color.

2 Drawing Sheets

Botanical designation: *Begonia×hiemalis.*
Cultivar denomination: 'BKPBEEEBP'.

BACKGROUND OF THE INVENTION

The present invention relates to a new and distinct cultivar of *Begonia* plant, botanically known as *Begonia×hiemalis*, commercially referred to as Elatior *Begonia* and hereinafter referred to by the name 'BKPBEEEBP'.

The new *Begonia* plant is a product of a planned breeding program conducted by the Inventor in Maasdijk, The Netherlands. The objective of the breeding program was to develop new freely branching and freely flowering *Begonia* plants with attractive double flowers.

The new *Begonia* plant is a naturally-occurring branch mutation of *Begonia×hiemalis* 'BKPBEEEP', disclosed in U.S. Plant Pat. No. 27,116. The new *Begonia* plant was discovered and selected by the Inventor on a single flowering plant within a population of plants of 'BKPBEEEP' in a controlled greenhouse environment in Maasdijk, The Netherlands in February, 2013.

Asexual reproduction of the new *Begonia* plant by vegetative tip cuttings in a controlled greenhouse environment in Maasdijk, The Netherlands since May, 2013 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEEBP'. These characteristics in combination distinguish 'BKPBEEEBP' as a new and distinct *Begonia* plant:

1. Broadly upright to outwardly spreading and mounded plant habit.
2. Freely basal branching habit.
3. Dark green-colored leaves.
4. Uniform and freely flowering habit.
5. Semi-double to fully double flowers with tepals and tepaloids that are bright red purple in color.

Plants of the new *Begonia* can be compared to plants of the female parent, 'BKPBEEEP'. Plants of the new *Begonia* differ primarily from plants of 'BKPBEEEP' in flower tepal and tepaloid color as plants of 'BKPBEEEP' have dark pink-colored flower tepals and tepaloids.

Plants of the new *Begonia* can be compared to plants of the *Begonia×hiemalis* 'Dragone', not patented. In side-by-side comparisons conducted in Maasdijk, The Netherlands, plants of the new *Begonia* differ from plants of 'Dragone' in the following characteristics:

1. Plants of the new *Begonia* have lighter green-colored leaves than plants of 'Dragone'.
2. Flowers of plants of the new *Begonia* have fewer tepals and tepaloids than flowers of plants of 'Dragone'.

Plants of the new *Begonia* can also be compared to plants of the *Begonia×hiemalis* 'Sweet Dreams', not patented. In side-by-side comparisons conducted in Maasdijk, The Netherlands, plants of the new *Begonia* differ from plants of 'Sweet Dreams' in the following characteristics:

1. Plants of the new *Begonia* have flatter tepals and tepaloids than plants of 'Sweet Dreams'.
2. Flowers of plants of the new *Begonia* are not fragrant whereas flowers of plants of 'Sweet Dreams' are slightly fragrant.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEEBP' grown in a container.

The photograph on the second sheet are close-up views of upper and lower surfaces of typical fully developed flowers and leaves of 'BKPBEEEBP'.

DETAILED BOTANICAL DESCRIPTION

Plants used for the aforementioned photographs and following observations and measurements were grown in 13-cm containers during the winter in a glass-covered greenhouse in Maasdijk, The Netherlands. During the production of the plants, day temperatures ranged from 19° to 20° C., night temperatures ranged from 18° to 19° C. and light levels averaged 7,000 lux. Plants were 13 weeks old when the photographs and the description were taken. In the following description, color references are made to The Royal Horticultural Society Colour Chart, 2015 Edition, except where general terms of ordinary dictionary significance are used.

Botanical classification: *Begonia×hiemalis* 'BKPBEEEBP'.

Parentage: Naturally-occurring branch mutation of *Begonia×hiemalis* 'BKPBEEEP', disclosed in U.S. Plant Pat. No. 27,116.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically light brown in color, actual color of the roots is dependent on substrate composition, water quality, fertilizer type and formulation, substrate temperature and physiological age of roots; plants of the new *Begonia* have not been observed to form tubers.

*Rooting habit*.—Moderate freely branching; medium density.

Plant description:

*Plant and growth habit*.—Broadly upright to outwardly spreading and mounded plant habit; plant shape roughly globular; freely branching with about three basal branches, each with about five lateral branches, developing per plant; moderately vigorous growth habit; moderate growth rate.

*Plant height, soil level to top of foliar plane*.—About 22.8 cm.

*Plant height, soil level to top of floral plane*.—About 27.3 cm.

*Plant width*.—About 32.5 cm.

*Lateral branch description*.—Length: About 12.3 cm. Diameter: About 9 mm. Internode length: About 2.9 cm. Strength: Moderately strong. Aspect: About 35° from the vertical. Texture and luster: Sparsely pubescent; glossy. Color, developing: Close to 152B. Color, fully developed: Close to 152A; at internodes, close to 178A to 178B.

*Leaf description*.—Arrangement: Alternate, simple. Length: About 13.1 cm. Width: About 9.2 cm. Shape: Ovate. Apex: Acute. Base: Oblique, slightly imbricate. Margin: Crenate; strongly undulate. Texture and luster, upper surface: Glabrous, slightly velvety; slightly glossy. Texture and luster, lower surface: Sparsely pubescent along veins; moderately glossy. Venation pattern: Laciniate. Color: Developing leaves, upper surface: Darker than between 143A and 146A. Developing leaves, lower surface: Close to 146B tinged with close to 177D. Fully expanded leaves, upper surface: Darker than between 139A and 147A; venation, close to 143A. Fully expanded leaves, lower surface: Close to 178A to 178B; venation, close to 144A. Petioles: Length: About 5.5 cm. Diameter: About 6 mm. Texture and luster, upper and lower surfaces: Sparsely pubescent; moderately glossy. Color, upper surface: Close to 152A to 152B; distally, close to 178A and 180A. Color, lower surface: Close to 152B; distally, close to 180A. Stipules: Quantity per leaf: Two. Length: About 1.2 cm. Width: About 1 cm. Shape: Broadly ovate. Apex: Obtuse. Base: Broadly cuneate. Margins: Entire. Color, upper and lower surfaces: Close to 145B; apex, close to 180C to 180D.

Flower description:

*Flowering habit*.—Semi-double to double rotate flowers arranged in axillary compound cymes; freely flowering habit with about five flowers per cyme and about 425 flowers developing per plant; flowers face upright to outwardly; only sterile male flowers have been observed on plants of the new *Begonia*.

*Fragrance*.—None detected.

*Natural flowering season*.—Plants begin flowering about 44 days after planting; long flowering period, plants flower freely and continuously from spring into the autumn in The Netherlands.

*Postproduction longevity*.—Individual flowers last about ten days on the plant; flowers not persistent; plants maintain good substance for about 20 to 30 days in an interior environment.

*Inflorescence height*.—About 12.9 cm.

*Inflorescence diameter*.—About 8.7 cm.

*Flower buds*.—Length: About 1.4 cm. Diameter, flattened: About 1.5 cm. Shape: Broadly obovate to roughly circular; flattened. Texture and luster: Glabrous, velvety; very slightly glossy. Color: Close to 47C.

*Male flowers*.—Diameter: About 5.3 cm. Depth: About 1.7 cm. Tepals: Quantity and arrangement: Four per flower, arranged in two whorls. Length, lower tepals: About 2.8 cm. Width, lower tepals: About 3.5 cm. Length, upper tepals: About 2.5 cm. Width, upper tepals: About 2.8 cm. Shape: Reniform. Apex: Rounded. Margin: Entire; slightly undulate. Texture and luster, upper surface: Glabrous, moderately velvety; matte. Texture and luster, lower surface: Glabrous; slightly velvety; lower tepals, slightly glossy and upper tepals, matte. Color: When opening, upper surface: Close to 61C; towards the margins, close to between 53C and N57A to N57B. When opening, lower surface: Close to 52B. Fully opened, upper surface: Close to N57A and 58B; color does not fade with development. Fully opened, lower surface: Close to 52B; towards the margins, close to 51A; color does not fade with development. Tepaloids: Quantity and arrangement: About three to 37 per flower, arranged in multiple whorls. Length: About 1.1 cm to 2.3 cm. Width: About 5 mm to 2 cm. Shape: Obovate. Apex: Rounded to shallowly cleft. Base: Attenuate. Margin: Entire; slightly undulate. Texture and luster, upper surface: Glabrous, moderately velvety; matte. Texture and luster, lower surface: Glabrous, slightly velvety; matte. Color: When opening, upper surface: Close to 61C; towards the margins, close to between 53C and N57A to N57B; base of smaller tepaloids tinged with close to 13A to 13B. When opening, lower surface: Close to 58B; base of smaller tepaloids tinged with close to 13A to 13B. Fully opened, upper surface: Close to N57A and 58B; base of smaller tepaloids tinged with close to 13A to 13B; color does not fade with development. Fully opened, lower surface: Close to 58B to 58C; towards the margins, close to 53D; base of smaller tepaloids tinged with close to 13A to 13B; color does not fade with development.

*Peduncles*.—Length: About 7.2 cm. Diameter: About 4 mm. Angle: About 30° from lateral branch axis. Strength: Moderately strong; flexible and bending with the weight of the flowers. Texture and luster: Glabrous; moderately glossy. Color: Close to 152B.

*Pedicels*.—Length: About 1.8 cm. Diameter: About 1.5 mm. Angle: About 35° from the peduncle axis. Strength: Moderately strong; flexible, bending with the weight of the flowers. Texture and luster: Glabrous; glossy. Color: Close to 179A to 179B.

*Flower bracts*.—Quantity and arrangement: Two per flower, opposite. Length: About 1.3 cm. Width: About 1.4 cm. Shape: Roughly orbicular. Margin: Entire. Texture and luster, upper and lower surfaces: Glabrous; matte. Color, upper surface: Close to 144A tinged with close to 180B. Color, lower surface: Close to 144A.

*Reproductive organs*.—Stamens: Quantity per flower: About three to 37. Filament length: About 7 mm. Filament color: Close to 25A to 25B. Anther size: About 1 mm by 0.5 mm. Anther shape: Elliptic. Anther color: Close to 12A. Pollen amount: None observed; sterile. Seeds and fruits: Seed and fruit development have not been observed on plants of the new *Begonia*.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKP-BEEEBP' as illustrated and described.

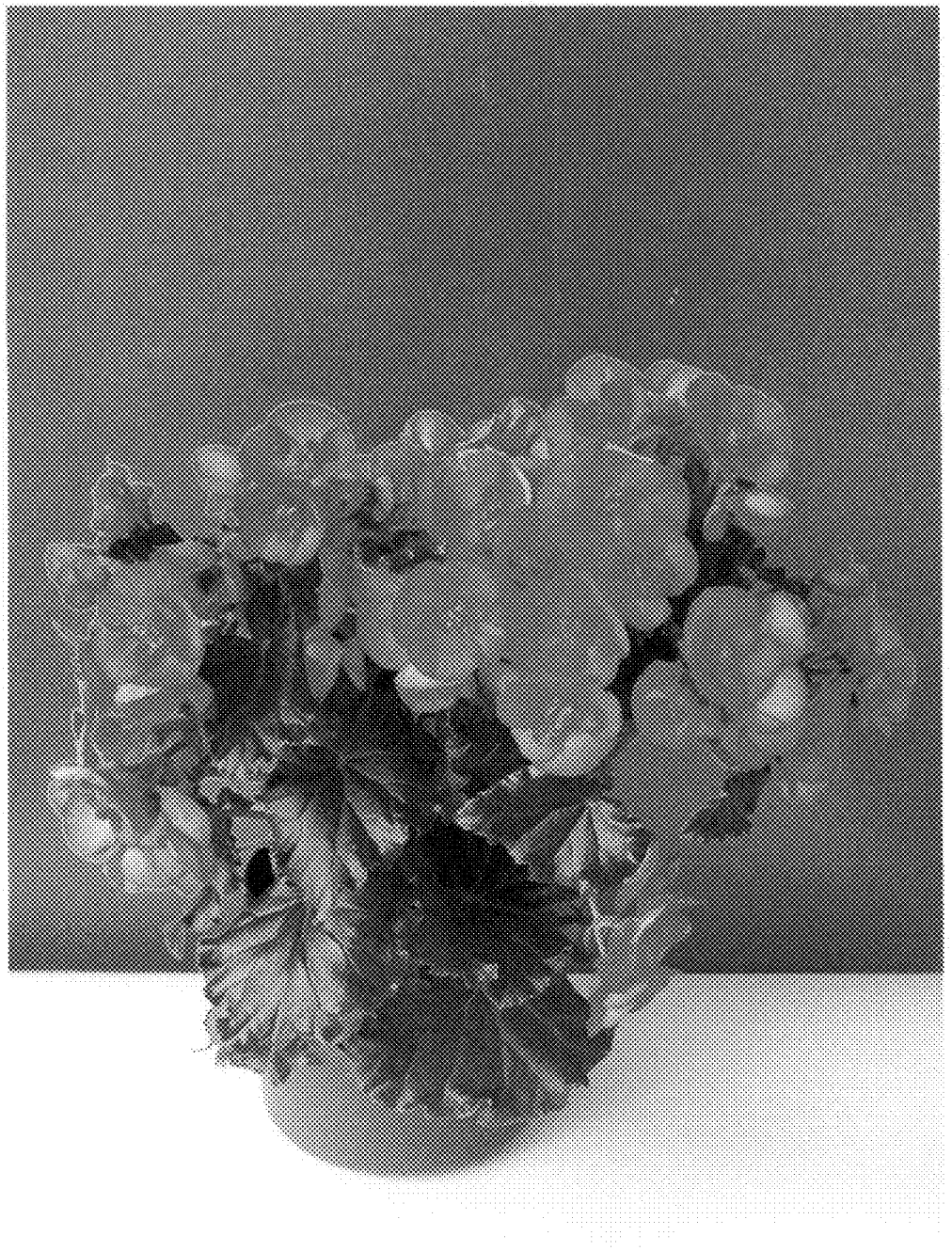

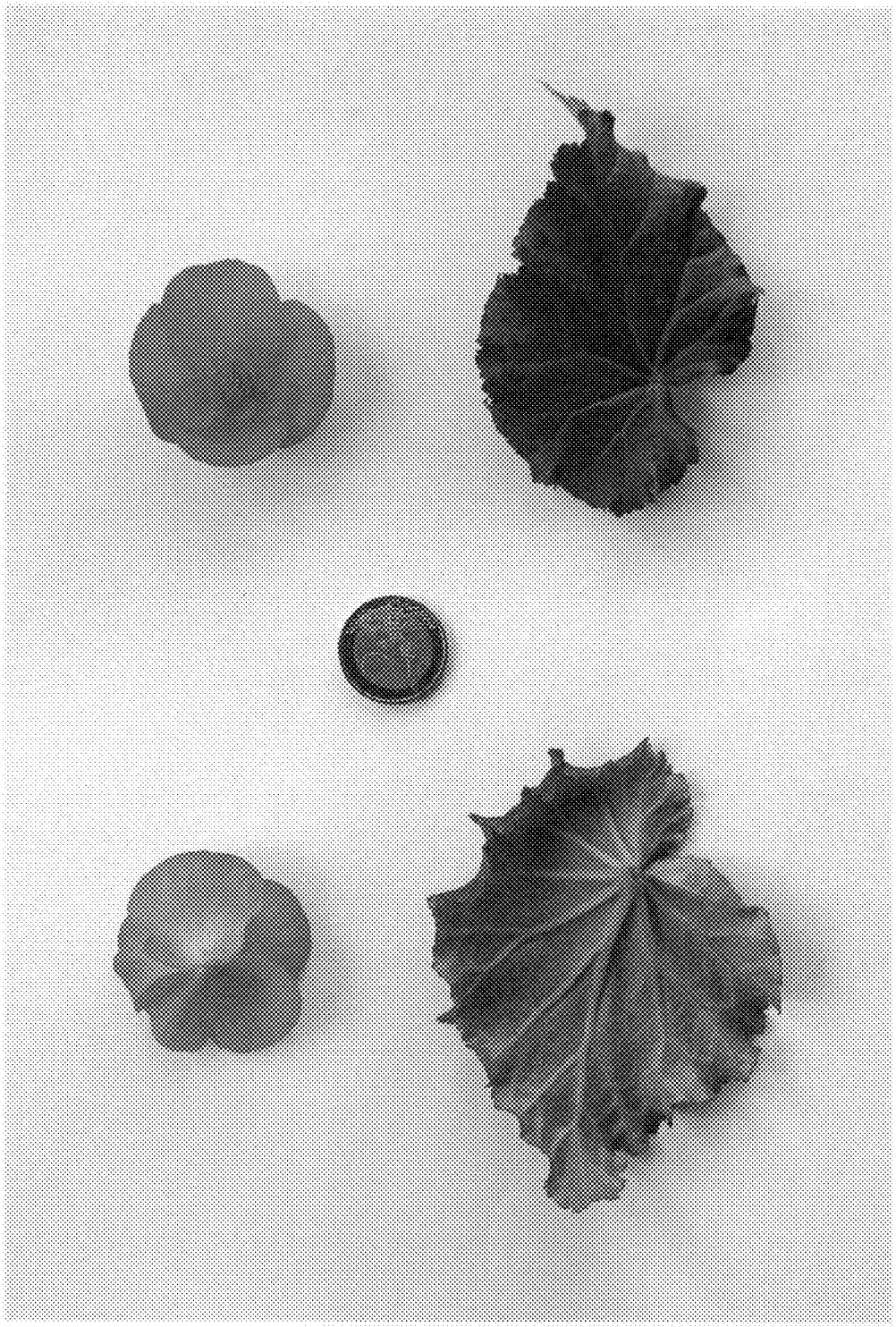

* * * * *